United States Patent
Wagner et al.

(10) Patent No.: US 8,012,081 B2
(45) Date of Patent: *Sep. 6, 2011

(54) ADJUSTABLE SURGICAL SLING

(75) Inventors: James Wagner, Sudbury, MA (US); Arthur Madenjian, Winchester, MA (US); Jamie Li, Lexington, MA (US)

(73) Assignee: Boston Scientific Scimed, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/755,099

(22) Filed: Apr. 6, 2010

(65) Prior Publication Data

US 2010/0198000 A1 Aug. 5, 2010

Related U.S. Application Data

(63) Continuation of application No. 11/217,554, filed on Sep. 1, 2005, now Pat. No. 7,699,769.

(51) Int. Cl.
*A61F 2/02* (2006.01)

(52) U.S. Cl. ........................................ 600/30

(58) Field of Classification Search .............. 600/29–32, 600/37; 623/23.64, 23.66, 23.67; 128/885
See application file for complete search history.

(56) References Cited

U.S. PATENT DOCUMENTS

| | | | |
|---|---|---|---|
| 6,770,025 B2 | 8/2004 | Zunker | |
| 6,786,861 B1 | 9/2004 | Pretorius | |
| 7,083,637 B1 | 8/2006 | Tannhauser | |
| 7,395,822 B1 * | 7/2008 | Burton et al. | 128/885 |
| 7,699,769 B2 * | 4/2010 | Wagner et al. | 600/30 |
| 2002/0183588 A1 | 12/2002 | Fierro | |
| 2004/0144395 A1 | 7/2004 | Evans et al. | |
| 2005/0055104 A1 | 3/2005 | Amal et al. | |
| 2005/0283040 A1 | 12/2005 | Greenhalgh | |
| 2007/0010807 A1 | 1/2007 | Chu | |
| 2007/0015955 A1 | 1/2007 | Tsonton | |

FOREIGN PATENT DOCUMENTS

| | | |
|---|---|---|
| DE | 1010380950 A1 | 2/2003 |
| DE | 10 2005 021893 A1 | 11/2006 |
| EP | 00639 355 A1 | 2/1995 |
| EP | 0677297 | 12/2000 |
| WO | WO 98/35632 A2 | 8/1998 |
| WO | WO 00/18319 | 4/2000 |
| WO | WO 00/66030 | 11/2000 |
| WO | WO 00/74633 | 12/2000 |
| WO | WO 02/19945 | 3/2002 |
| WO | WO 03/007847 | 1/2003 |

\* cited by examiner

*Primary Examiner* — Charles A Marmor, II
*Assistant Examiner* — Christine D Hopkins
(74) *Attorney, Agent, or Firm* — Bingham McCutchen LLP

(57) ABSTRACT

The invention, in one embodiment, is directed to systems and methods for adjusting support to an anatomical location using an expandable chamber.

21 Claims, 6 Drawing Sheets

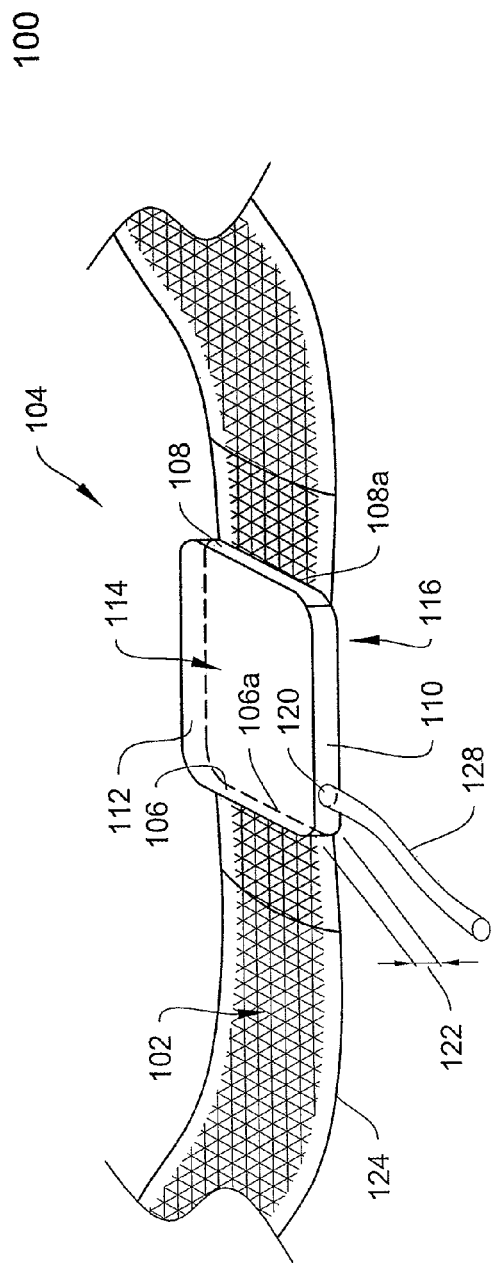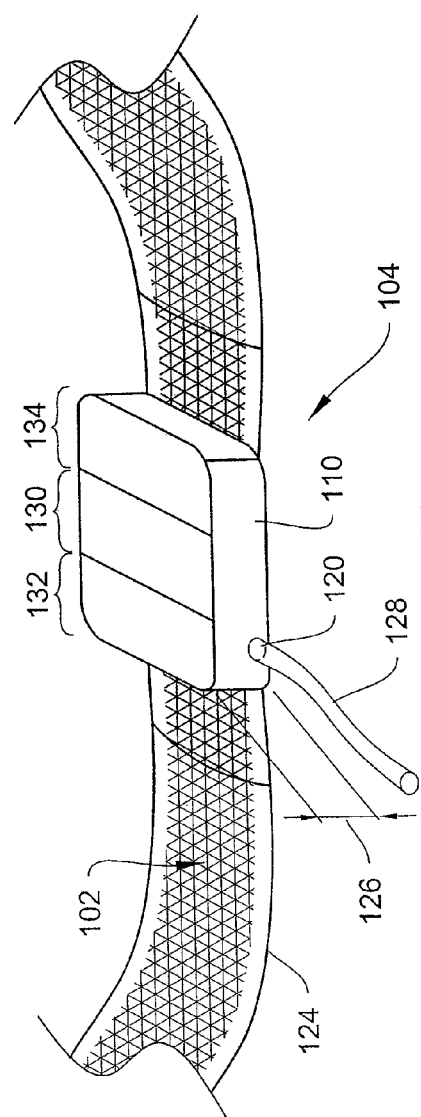

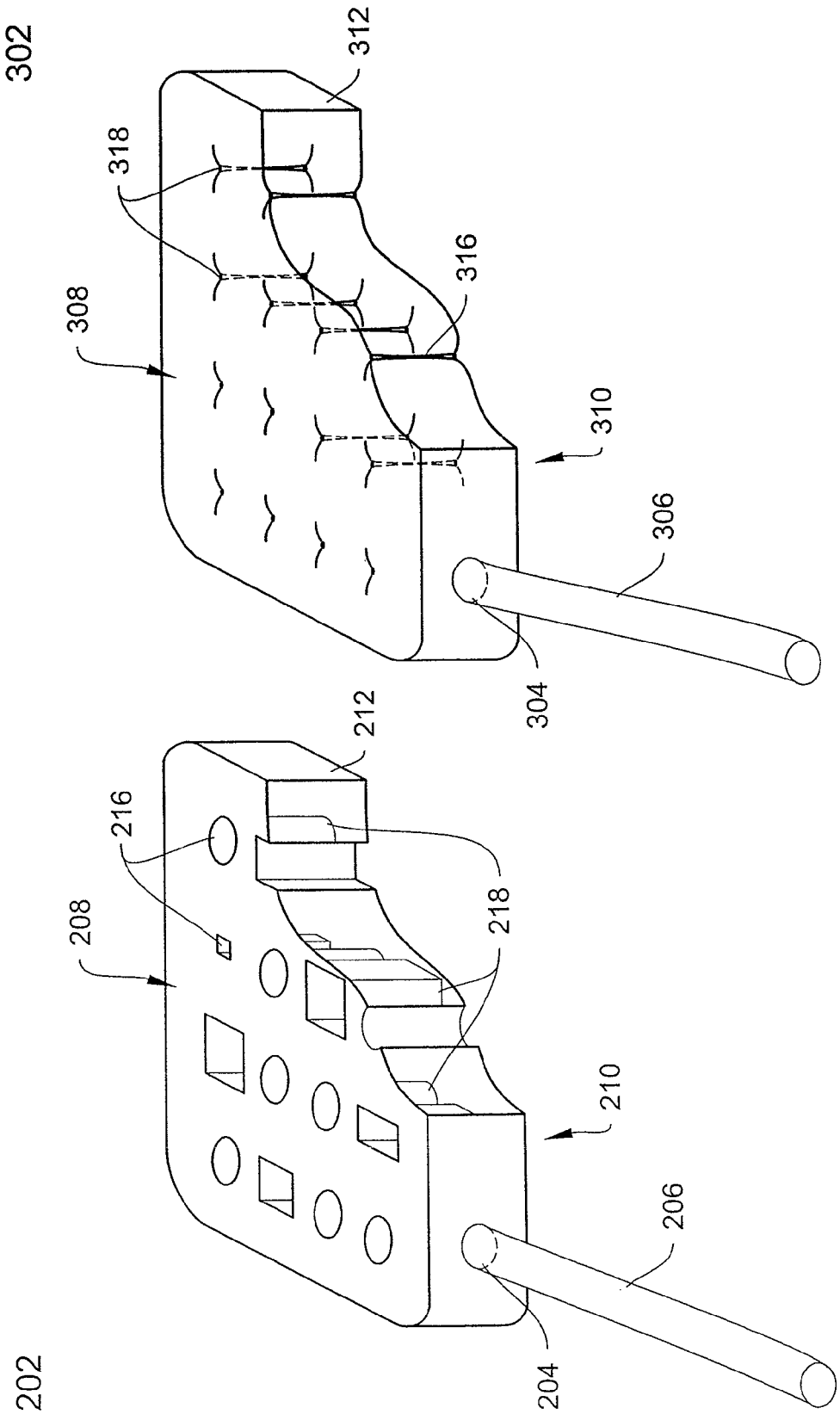

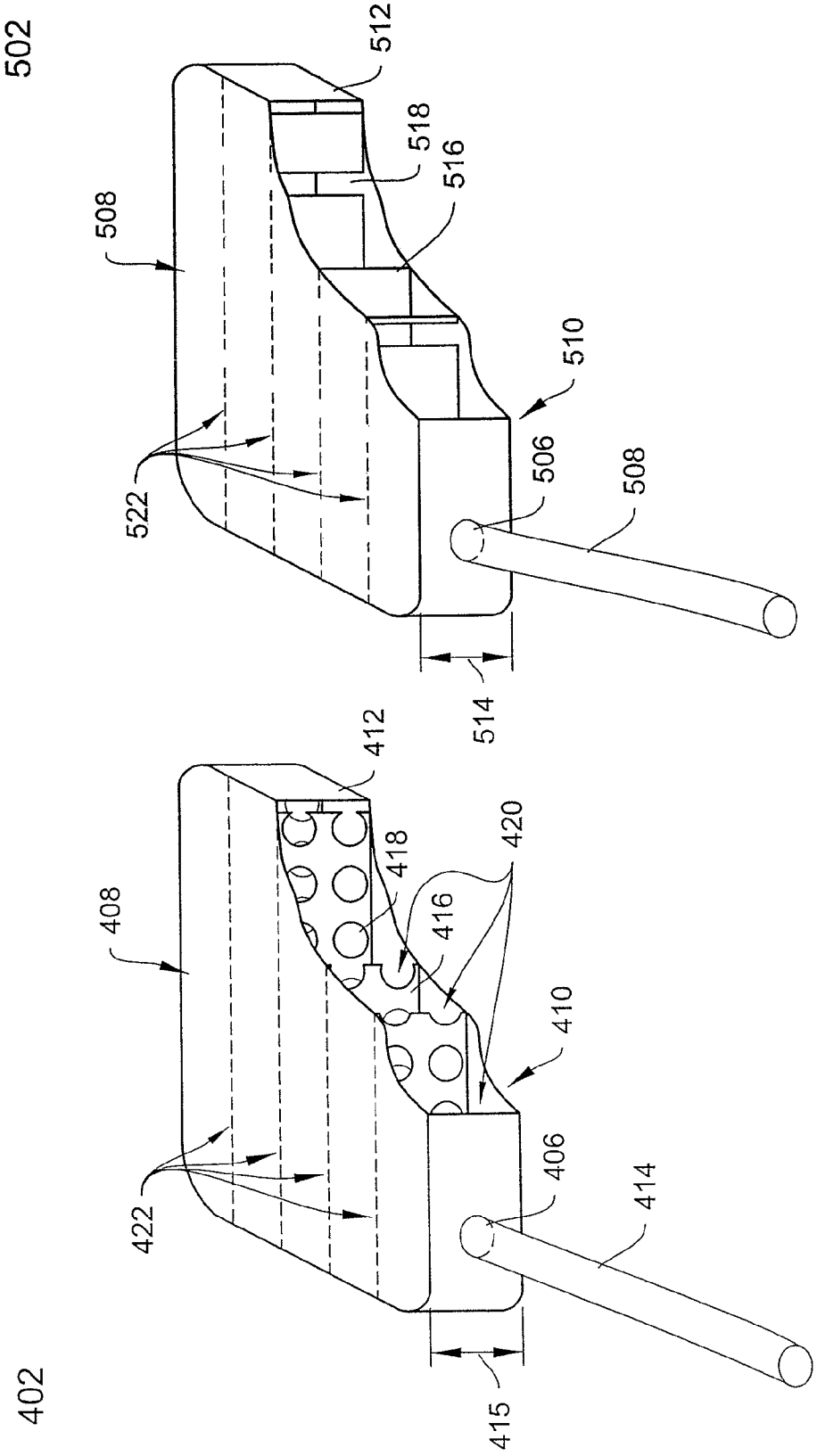

ADJUSTABLE SURGICAL SLING

This application is a continuation of application Ser. No. 11/217,554, filed on Sep. 1, 2005 now U.S. Pat. No. 7,699,769, all of which is incorporated herein by reference in its entirety.

FIELD OF THE INVENTION

The invention generally relates to surgically implantable slings. More specifically, in various embodiments, the invention is directed to a surgically implantable sling having an expandable supportive chamber.

BACKGROUND

Urinary incontinence affects over 13 million men and women of all ages in the United States. Stress urinary incontinence (SUI) affects primarily women and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). The result is that there is an insufficient response time to promote urethral closure and, consequently, urine leakage and/or flow results.

A popular treatment of SUI is the use of a sling, which is permanently placed under a patient's bladder neck or mid-urethra to provide a urethral platform. Placement of the sling limits the endopelvic fascia drop, while providing compression to the urethral sphincter to improve coaptation. Generally, the sling is surgically placed under urethra or bladder neck, close to the high-pressure zone with no elevation of the urethra. When abdominal pressure increases, the sling stops the descent of the urethra and functions as a mechanism of closure for the urethra to prevent urine leakage. However, if too much tension is applied, the patient may go into urine retention, unable to void the bladder and suffer a pressure build-up in the bladder. Such pressure build-up can lead to reflux of urine up the ureters and into the kidney, eventually resulting in kidney damage, and, potentially, kidney loss. If the tension is too small, the implanted sling may not perform its function as intended. Clinically, there is technical challenge to position and apply the correct tension to the sling. Therefore, it is sometimes necessary to modify the sling tension after the implantation surgery of the sling. Currently, there is no easy method to adjust the tension of the sling to compensate for the tension change of the sling over time. Therefore, improved surgically implantable slings, and methods to adjust the sling tension are needed.

SUMMARY OF THE INVENTION

The invention provides, in various embodiments, devices and methods relating to surgically implantable slings. In one aspect, the invention provides a surgically implantable sling for the treatment of urinary incontinence, which includes an expandable chamber intermediate to the two ends of the sling, in a portion of the sling that supports the urethra. The chamber, in one configuration, is shaped and sized such that the top surface of the chamber, which touches the urethra when sufficiently inflated, is generally flat, giving the chamber a substantially rectangular cross-sectional outline. The chamber may be filled to varying degrees by injecting or removing a filling materials into or from the chamber. Depending on the degree of fullness of the chamber, the height of the chamber changes, thus changing the position of the top surface of the chamber relative to the urethra. According to another feature, the changes in chamber height change the degree to which the sling generally and the top surface of the chamber specifically support the urethra. According to a related feature, changing the chamber height causes tensioning of the sling to change.

According to some configurations, at least the portion of the top surface supporting the urethra is maintained at approximately the same or a lower height than that of peripherally located portions of the top surface that do not contact the urethra, even when the chamber is in various states of expansion. In this way, the invention reduces the likelihood of the urethra rolling or sliding off the top surface of the chamber. It also reduces the likelihood of the chamber being displaced in such a way that the sling no longer properly supports the urethra. Although these height features are described in terms of reducing the likelihood of a urethra rolling or sliding off the top surface of the chamber, such features are equally applicable to supporting any anatomical location or feature.

In one embodiment, the expandable chamber has one or more through passages connecting the upper side and the lower side of chamber, externally giving the chamber a perforated configuration. More particularly, in one configuration, the through passages extending between the upper and lower sides form one or more walls that extend between and connect inner surfaces of the upper and lower sides of the chamber. According to one feature of this configuration, the perforations facilitate tissue in growth for effectively anchoring the chamber at a mid-urethral location. According to another feature, the walls extending between and connecting the inner surfaces of the upper and lower sides of the chamber cause the outer surface of the upper side to be substantially flat except for the through passages. According to a further feature, the walls extending between and connecting the inner surfaces of the upper and lower sides of the chamber maintain a middle portion of the top surface of the upper side at approximately the same or a lower height than a peripherally located portion of the top surface, even when the chamber is expanded.

In another embodiment, the expandable chamber is divided by at least one divider into sub-chambers that are in fluid communication with each other. The divider extends between the inner surfaces of the upper and lower sides, and in certain embodiments, the dividers intersect with one another. In another illustrative embodiment, the expandable chamber includes cord-like material extending between and connecting the upper and lower sides internal to the chamber.

In an alternative illustrative embodiment of the invention, the upper side of the expandable chamber is substantially rigid. In another illustrative embodiment, the expandable chamber has at least a pair of opposing sides, each of their top and bottom edges are attached to the edges of the upper side and the lower side, respectively. The sides have accordion-like structures for expanding and contracting to increase and/or decrease the height of the expandable chamber, in response to the chamber being inflated or deflated, respectively.

The expandable chamber of the sling assembly according to the invention can be constructed, at least in part, from a self-sealing material. The filler material can be injected directly into the chamber through the self-sealing material. In another embodiment, the expandable chamber includes a port, from which a filler material can be introduced into or removed from the expandable chamber. In certain embodiments, the port is located on the chamber. According to one feature, the port includes an extension that extends away from the chamber, providing fluid access at a location other than where the expandable chamber is located. In an example of such an embodiment, the extension end farthest from the chamber is positioned in an anatomical location of the patient when implanted in a patient, so that the end of the extension end, from which the filling material is injected or withdrawn, is easily accessible using no or minimally invasive procedures.

The expandable chamber can be sized and shaped so that it may be filled with a variety of materials. Filler materials suitable to be used in the present invention are sterile, biocompatible and can be either inert or therapeutically active. The filler materials can be selected from various gas, liquid, gel, slurry, and/or phase-changing materials.

Another aspect of the invention provides a sling assembly with an expandable chamber formed at least in part from permeable material. Part or all of the expandable chamber may be made from permeable material to allow certain components of the filler material to be released into the tissue environment surrounding the implanted sling. The chamber may be filled with a filler material including, for example, a therapeutic agent, which may be, for example, an analgesic or an anti-inflammatory drug, a biological, a growth factor, a hormone, a genetic material, a biologically active agent that is beneficial to the patient, or any other suitable agent. Components of the filler material may be released from the chamber through the permeable material.

In another aspect, the invention provides a method for adjusting support for a urethra including the step of adjusting the inflation of an expandable chamber in a patient to provide a stable platform for supporting the urethra. The expandable chamber may have any or all of the characteristics described above. The method may also include the step of adjusting the degree to which the chamber is expanded from a port located at an easily accessible location spaced away from the location of the sling assembly.

The patient may be sitting or standing so that the torso is in a position where most of the daily activities occur, in contrast to being prostrate as is typically the case during the surgery for implanting a sling assembly. Adjusting the sling tension while the patient's torso is substantially upright allows determining the most suitable support of the urethra while the patient is engaged in everyday activities. The minimally invasive nature of the method of the invention makes such adjustment possible.

BRIEF DESCRIPTION OF THE DRAWINGS

The following figures depict certain illustrative embodiments of the invention in which like reference numerals refer to like elements. These depicted embodiments may not be drawn to scale and are to be understood as illustrative of the invention and not as limiting in any way.

FIGS. 1A, 1B, and 1C depict a front perspective view of a sling assembly having an expandable chamber in a contracted state (1A) and expanded state (1B) and an expanded state of an alternative configuration (1C), respectively, according to illustrative embodiments of the invention.

FIG. 2 is a perspective cutaway view of an expandable chamber includes through channels having walls connecting the upper and lower sides of the chamber according to an illustrative embodiment of the invention.

FIG. 3 is a perspective cutaway view of an expandable chamber having cord-like structures connecting internal surfaces of the upper and lower sides of the chamber according to an illustrative embodiment of the invention.

FIG. 4 is a perspective cutaway view of an expandable chamber having dividers connecting internal surfaces of the upper and lower sides of the chamber and forming sub-chambers that are in fluid communication with each other according to an illustrative embodiment of the invention.

FIG. 5 is a perspective cutaway view of an expandable chamber with non-contiguous dividers connecting inner surfaces of the upper and lower sides of the chamber and forming sub-chambers that are in fluid communication with each other according to an illustrative embodiment of the invention.

DESCRIPTION OF ILLUSTRATIVE EMBODIMENTS

Figure 1C:
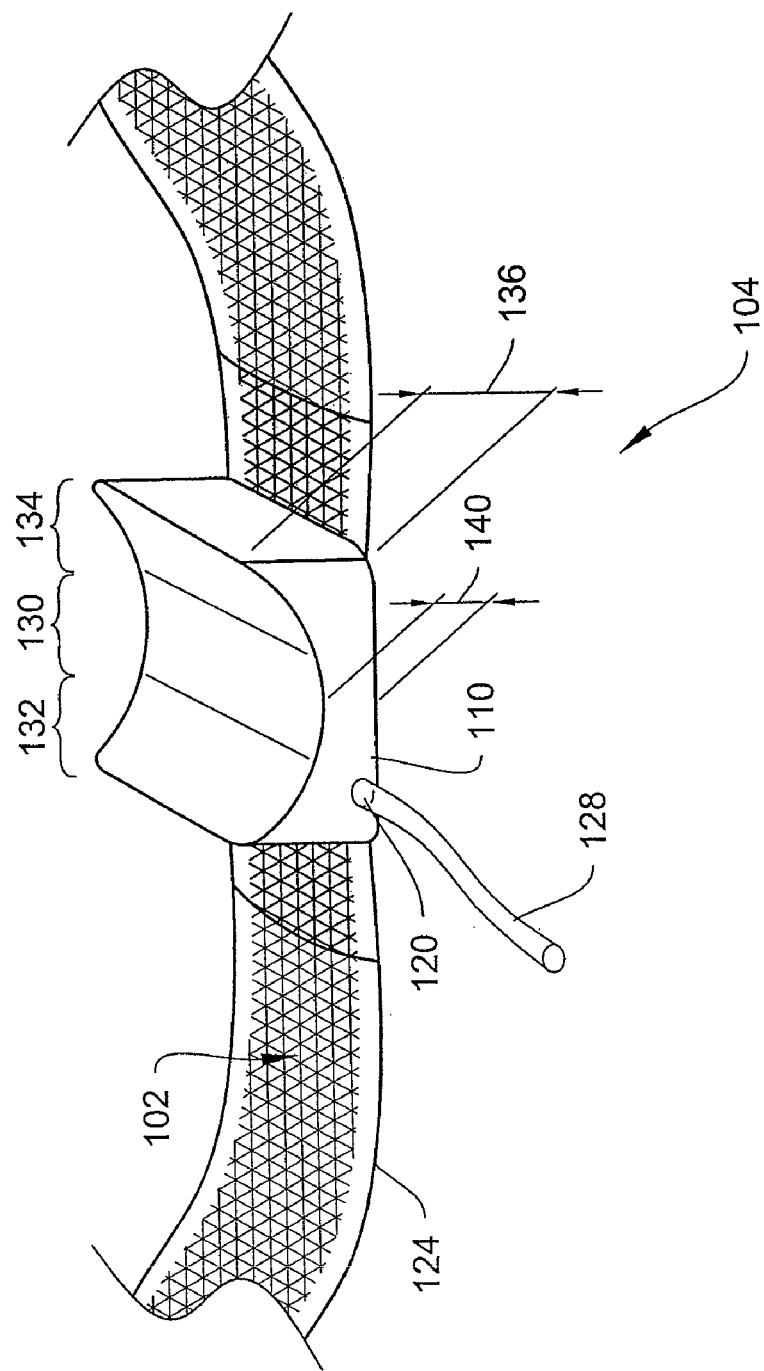

As described above in summary, the invention in various embodiments is directed to systems, methods, devices and assemblies relating to an expandable chamber for supporting an anatomical site in a patient. FIGS. 1A and 1B depict a front perspective view of a portion of a sling assembly 100 having an expandable chamber 104 according to an illustrative embodiment of the invention. More particularly, FIG. 1A shows the expandable chamber 104 in a contracted state, while FIG. 1B shows the expandable chamber 104 in an expanded state.

The illustrative sling assembly 100 includes a sling 102 and a sleeve 124, which encloses, at least partially, the sling 102. The expandable chamber 104 includes a top side 114 and a bottom side 116. The expandable chamber 104 also includes axially extending front 110 and back 112 walls, along with two transversely extending side walls 106 and 108. The walls 106, 108, 110, and 112 extend between the top 114 and bottom 116 sides to form the expandable chamber 104. Although the walls 106, 108, 110 and 112 are depicted as being a single substantially continuous and substantially square wall, this need not be the case. For example, one or more of the walls 106, 108, 110 and 112 may include a curved section, or may be formed as a continuous oval or circular wall. Additionally, they may be formed as individual structures bonded together in any suitable fashion. The expandable chamber 104 may also include more than four walls extending between the top 114 and bottom 116 sides, for example, five, six, seven or eight walls. Additionally, the walls 106, 108, 110 and 112, in some embodiments, extend between inner surfaces of the top 114 and bottom 116 sides. In other embodiments, one or more portions of the chamber 104 may be molded as a unitary structure.

According to the illustrative embodiment, the expandable chamber 104 is approximately 1 cm wide and about 1 cm to about 6 cm long, with the thickness (height) dimension 122 of about 1 mm when in a non-expanded state (FIG. 1A) and a thickness dimension 126 of up to about 10 mm (FIG. 1B) when in an expanded state. In one preferred embodiment, the chamber 104 has a thickness dimension 126 within the range of about 3 mm to about 7 mm when in the expanded state. The expandable chamber 104 has substantially rectangular cross section taken both axially and transversely. In another embodiment as depicted in FIG. 1C and described below in the next paragraph, the expandable chamber 104 has a transverse cross section may have a substantially planar or "U" shaped bottom edge and a "U" shaped top edge with two side edges connecting the bottom edge and the top edge. It should be noted that the above dimensions are particularly well suited for supporting a urethra or bladder neck for treating urinary incontinence, and that other suitable dimensions may be employed depending on the anatomical site to be supported with the sling assembly 100.

According to one illustrative embodiment, the expandable chamber 104 is formed from any suitable biocompatible material and is constructed such that the chamber 104 expands substantially evenly and maintains the top side 114 substantially flat. One objective of maintaining the top side 114 substantially flat is to discourage an anatomical site supported by the chamber 104 from rolling or sliding off the top side 114. According to a related embodiment, the top side 114 may be conceptually divided into three regions: two axially peripheral regions 132 and 134; and an axially central region 130 located between the two axially peripheral regions 132 and 134. In one configuration, the central region 130 includes the portion of the top side 114 that directly contacts the anatomical site to be supported. According to the illustrative embodiment, the axially central region 130 is maintained at a height 140 which is less than or equal to the height 136 of both axially peripheral regions 132 and 134 (FIG. 1C). When the axially central region 130 is depressed in relation to the axial peripheral regions 132 and 134 of the top 114, the top 114 forms a "U" shape of various depths of depression. According to embodiment, this height relationship is maintained when the chamber 104 is fully expanded. According to another embodiment, this height relationship is maintained during all states of chamber 104 expansion. The above described height relationship ensures that any anatomical site supported by the central region 130 will tend to slide or roll toward the center of the top side 114 rather than toward the periphery, where it would be more likely to slide or roll off the top side 114. According to other illustrative configurations, the same or a similar height relationship may exist laterally across the expandable chamber 104.

Figure 7:
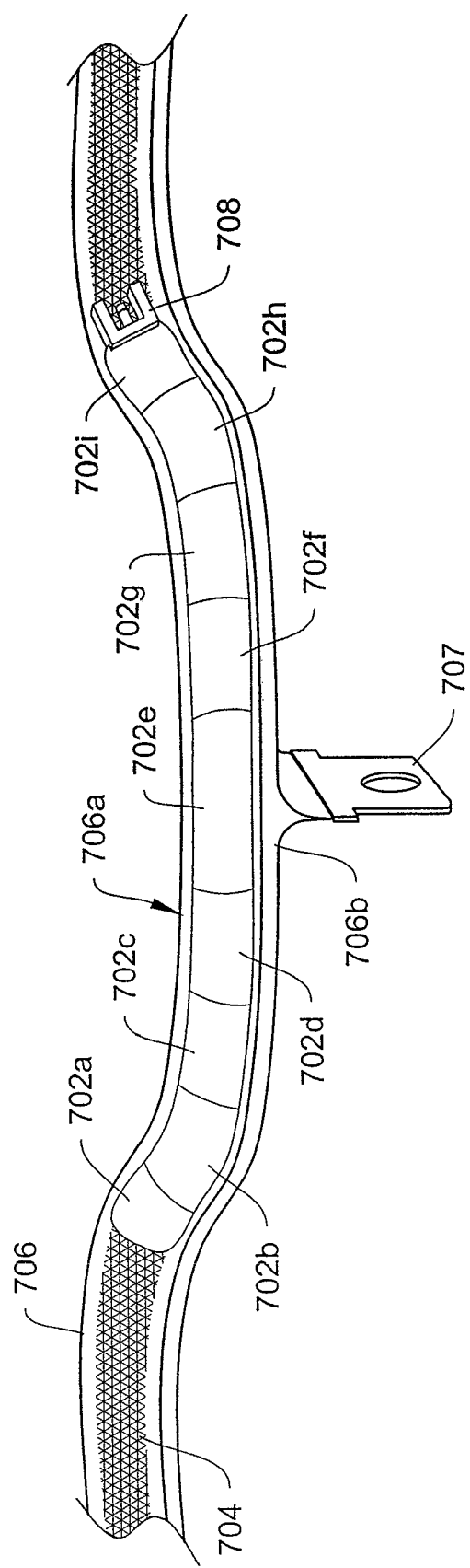
FIG. 7 is a front perspective view of a section of a sling assembly including an expandable chamber according to an illustrative embodiment of the invention.

The expandable chamber 104 may be attached to the sling 102 by any suitable mechanism including, but not limited to gluing, heat bonding, stitching, anchoring (see e.g. FIG. 7.) In the illustrative embodiment of FIGS. 1A and 1B, the expandable chamber 104 is glued to the bottom side 116 of expandable chamber 104. The sleeve 124, in the depicted embodiment, does not attach to the expandable chamber 104. Instead, the sleeve 124 has a gap along its top side, at least large enough to accommodate the expandable chamber. The sleeve 124 may include a similar gap along its bottom side, or alternatively, pass continuously under, but not bond to, the middle portion of the sling 102 and the bottom side 116 of the expandable chamber 104.

As shown in FIGS. 1A and 1B, the illustrative expandable chamber 104 includes a port 120 from which a filler material can be introduced into or removed from the expandable chamber 104. The filling port 120 may include an attached valve or a patch of self-sealing material. The valve is preferably a one-way valve to prevent undesired leakage of the filler material. According to some illustrative embodiments, a suitable syringe having a distal end sized and shaped to mate with and/or penetrate through the port 120 may be employed to insert the filler material into and/or remove the filler material from the expandable chamber 104.

The chamber 104, the port 120, and/or the suitable syringe are preferably constructed of radio-opaque materials, or include radio-opaque indicators, so that their location can be detected while the volume of the chamber 104 is adjusted by injecting or withdrawing the filler material. According to another illustrative embodiment, the expandable chamber 104 is constructed, at least in part, from a self-sealing material such as a silicone elastic. In this illustrative embodiment, the filler material may be added or removed from the chamber 104 via a syringe directly inserted into the chamber through the self-sealing material, without the need for a port, such as the port 120.

According to a further illustrative embodiment, and as depicted in FIGS. 1A and 1B, the expandable chamber 104 may include a port extension 128. When the sling assembly 100 is placed in a patient, it may be difficult to access the port 120 due to the location of the anatomical site being supported. The port extension 128 provides a fluid channel between the port 120 and an anatomical location remote from the anatomical site being supported by the chamber 104. Preferably, the port extension 128 leads to an anatomical location of the patient that is easily accessible with a minimally invasive or noninvasive procedure. In one example, the port extension 128 extends from the port 120 to a perineal area and may be accessed percutaneously via a syringe needle. In another example, the port extension 128 extends from the port 120 to the surface of the patient's body and can be accessed directly. The port extension 128 may be formed with materials suitable for catheters.

Any one or more of a plurality of filler materials may be employed with the expandable chamber 104 of the invention. Examples of suitable filler materials are preferably biocompatible, sterile, and can be either inert or therapeutically active. The filler materials can be selected, for example, from gas, liquid, gel, slurry, or phase-changing materials. An example of a filler material that is a gas is sterilized air. Another example of a filler material is sterilized saline. The filler material may also include materials that may solidify or liquefy depending on added chemicals and/or temperature changes. These materials include, for example, alginates, silicone fluid and gels, or Pluronic® F127.

In any of the foregoing illustrative examples or in any of the illustrative embodiments discussed below with regard to FIGS. 2-7, the expandable chamber 104 may be formed at least in part from permeable material. The permeable material allows certain components of the filler material to be released into the tissue environment surrounding the implanted sling. The components of the filler material to be released may include, for example, chemicals such as therapeutic agents, such as analgesics, antibiotics, and anti-inflammatories, and/or biologicals, such as a growth factor, a hormone, a genetic material, and/or any biological or chemical agent that is beneficial to the patient. According to another illustrative embodiment, the filler material that is released from the chamber 104 may be biologically inert and simply be a by-product of reactions of the filler material, such as water released in solidification of alginate by the addition of calcium.

Any of the sling assemblies described herein may also be coated with a therapeutic agent, such as an analgesic, an anti-inflammatory, an anti-biotic, a growth factor, a hormone, a genetic material, or any biologically active agent that is beneficial to the patient.

Additional illustrative embodiments of the invention will now be described with reference to FIGS. 2 through 7. FIG. 2 depicts a cutaway view of an expandable chamber 202 in its expanded state. The chamber 202 has through channels 216 connecting the external surfaces of the upper side 208 and the lower side 210. The through channels 216 may be round, square, rectangular, or any suitable shape, and they need not be of a uniform shape or size, nor be evenly distributed throughout the chamber 202. The chamber 202 also may have a port 204, with an optional extension tube 206. The port 204 and extension tube 208 are of the type described with respect to the port 120 and port extension of FIGS. 1A and 1B. The upper side 208 and the lower side 210 are constructed of materials that are flexible and may be expandable. According to the illustrative embodiment, the material forming walls 218 of the through channels 216 is resilient and flexible. Preferably, when the expandable chamber 202 is in a non-expanded state, such as shown in FIG. 1A, the walls 218 of the through channels 216 contract and act to pull the upper 208 and lower 210 sides together. As the chamber 202 expands, the walls 218 of the through holes 218 stretch, but continue to exert a force tending to pull the top 208 and bottom 210 walls together. Such construction results in an even increase in thickness dimension (e.g., 122 and 126 of FIGS. 1A and 1B) of the chamber 202. As described above with respect to FIGS. 1A and 1B, such construction maintains the chamber 202 in a condition that discourages an anatomical site, such as a urethra being supported by the chamber 202, from rolling or sliding off the upper side 208. Another advantage of the illustrative embodiment of FIG. 2 is that the through channels 216 allow tissues to grow into, around and through the chamber 202, thus tending to stabilize and integrate the chamber 202 and any sling to which it is attached into the body of the patient.

FIG. 3 shows a cutaway view of an expandable chamber 302 according to another illustrative embodiment of the invention. The expandable chamber 302 includes upper and lower sides 308 and 310, respectively, one or more side walls 312, a port 304, and optionally, a port extension 306.

The expandable chamber 302 of FIG. 3 operates substantially like the above described embodiments of FIGS. 1A, 1B and 2. However, instead of the through channels 216 of FIG. 2, the expandable chamber 302 employs one or more cord-like structures 316 for attaching inner surfaces of the upper 308 and lower 310 sides. The cord-like structures 316 operate in a similar fashion to the through channels 216 to achieve a chamber configuration that discourages an anatomical site being supported from rolling or sliding off the upper side 308. In some illustrative embodiments, the cord-like structures 316 are all substantially the same length to achieve a substantially flat upper side 308, excluding minor indentations 318 caused in the upper side 308 by cord connection locations. However, in other illustrative embodiments, the lengths of the cord-like structures 316 may vary to create, for example, a reduced thickness intermediate portion in the expandable chamber 302, such as that discussed above with respect to the intermediate portion 130 of FIG. 1. The cord-like structures 316 may be formed from the same or similar materials employed for the walls 218 of the through channels 216, and with similar results.

FIG. 4 shows a cutaway view of another embodiment of an expandable chamber 402 in an expanded state. The expandable chamber 402 includes one or more internal dividers 416 that extend between inner surfaces of its upper 408 and lower 410 sides, creating sub-chambers 420. The sub-chambers 420 are not isolated from each other, but instead are in fluid communication through the openings 418 in the dividers 416. The openings 418 enable a filler material to disperse evenly between the sub-chambers 420 so that the expandable chamber 402 expands evenly. This feature also causes the expandable chamber 402 to contract evenly in response to filler material being removed, for example, by way of the port 406 and, optionally, by way of the port extension tube 414. The openings 418 can be of any shape or size, as long as they allow sufficient fluid communication between the sub-chambers 420 for the filler material to flow.

The internal dividers 416 operate in a similar fashion to the through channels 216 to achieve a chamber 408 configuration that discourages an anatomical site being supported from rolling or sliding off the upper side 408. In some illustrative embodiments, the dividers 416 are all substantially the same height to achieve a substantially flat upper side 408, excluding minor indentations 422 caused in the upper side 408 by divider connection locations. However, in other illustrative embodiments, the heights of the dividers 416 may vary to create, for example, a reduced thickness intermediate portion in the expandable chamber 402, such as that discussed above with respect to the intermediate portion 130 of FIG. 1.

FIG. 5 shows a cutaway view of an expandable chamber 502 according to another illustrative embodiment of the invention. As shown in FIG. 5, in a similar fashion to the dividers 416 of FIG. 4, the dividers 516 extend between the upper side 508 and the lower side 510 of the expandable chamber 502. In place of the openings 418, the expandable chamber 502 employs gaps 518 interrupting each of the dividers 516 so that they do not extend contiguously across the expandable chamber 502, but instead are a series of short dividers with space in between each neighboring divider. The gaps 518 provide a path through which filler material may flow to provide substantially uniform expansion and contraction of the expandable chamber 502. Alternatively, the chamber dividers may be formed from a material sufficiently permeable to enable the filler material to flow between the sub-chambers. In such case the dividers may extend contiguously across the expandable chamber. As in the case of previously discussed embodiments, the expandable chamber 502 may include a port 506, which may be extended with a tube structure 508.

Figure 6B:
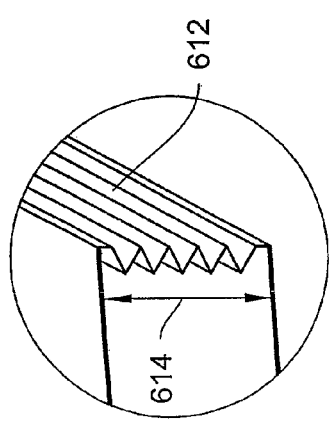
FIGS. 6A-6C depict various views of an expandable chamber having accordion-like sides connecting the upper and lower sides of the chamber according to an illustrative embodiment of the invention.
Figure 6C:
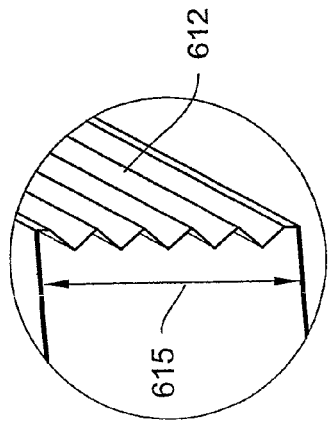
Figure 6A:
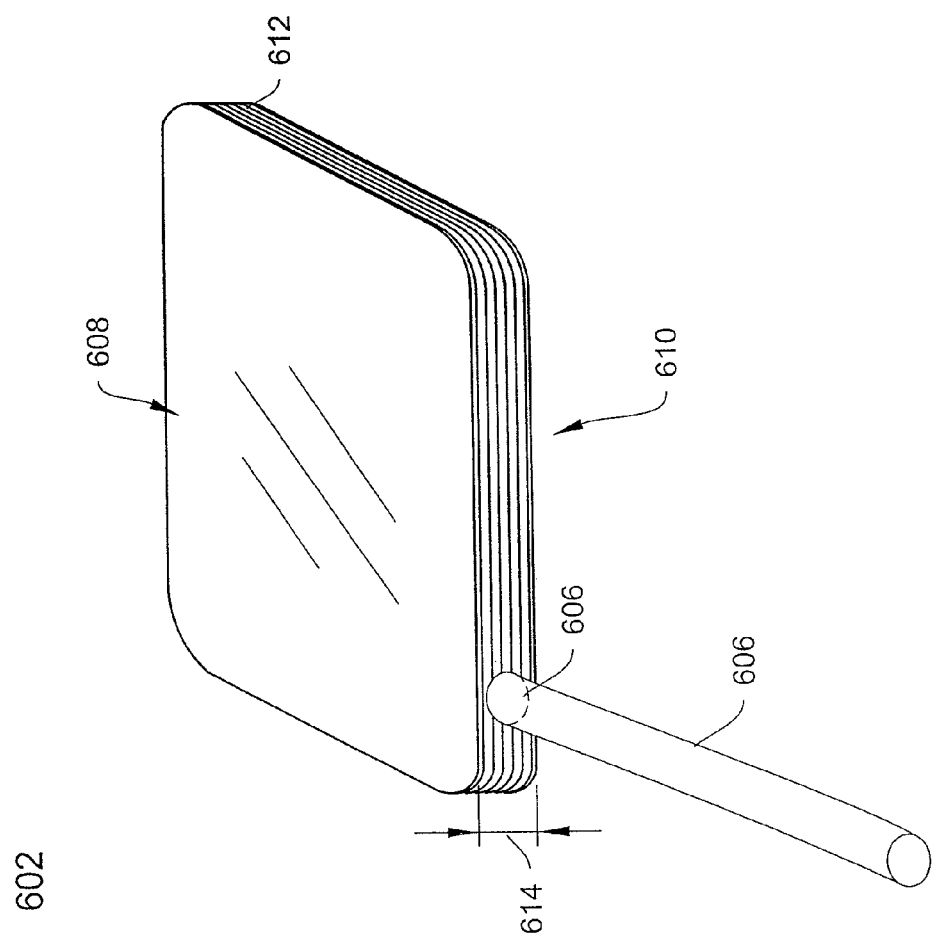

FIG. 6A shows a front perspective view of an expandable chamber 602 having one or more accordion-like sides 612 according to another illustrative embodiment of the invention. FIG. 6B shows a magnified perspective view of a section 614 of the side 612 in a relatively contracted state. FIG. 6B shows a magnified perspective view of the side section 614 in a relatively expanded state. As in the case of the previously discussed illustrative embodiments, the expandable chamber 602 includes upper 608 and lower 610 sides, along with a side wall 612 extending between the upper 608 and lower 610 sides. As also in the case of the previously discussed embodiments, the side wall 612 may be formed as a plurality of discrete walls or as a continuous wall. The illustrative expandable chamber 602 optionally includes a port 606 for inserting and removing filler material. The expandable chamber 602 also optionally includes a port extension 608, previously described. As illustrated in FIGS. 6B and 6C, as filler material is added into the chamber 602, the accordion-like structure of the side wall 612 expands from a height 614 to a height 615. In response to filler material being removed, the side wall contracts to a lower height. Any of the above discussed internal structures with respect the expandable chambers of FIGS. 1-5, for example, for exerting a forced to pull the upper 608 and lower 610 sides together during filler removal, may be employed with the expandable chamber 602 of FIGS. 6A-6C.

FIG. 7 depicts a section of a sling assembly 700 including an expandable chamber 702 according to another illustrative embodiment of the invention. As in the case of the sling assembly 100 of FIG. 1, the sling assembly 700 includes a mesh sling 704 and a protective sleeve 706 enclosing, at least partially, the sling 704. The protective sleeve 706 includes an upper side 706a and a lower side 706b, between which the sling 704 is situated. The upper side 706a of the sling 706 includes a discontinuity located along its length. The sling assembly 700 includes a tab 706 enclosing a looped portion of the lower side 706b of the sleeve 706. Cutting through the tab 706 and thus, the looped portion of the lower side 706b, separates the sleeve 706 into two halves, which may be slide off the sling 704. According to one feature, the sling assembly 700 includes a valve 708 on one end of the expandable chamber 702. The valve is so located that it will not come into contact with an anatomical location that the sling assembly supports when placed in a patient. As shown, the expandable chamber 702 may have an elongated configuration and include axially distributed sub-chambers 702a-702i, which may be in fluid communication for even expansion and contraction. Alternatively, the sub-chambers 702a-702i, along with any of the above discussed sub-chambers, may be expanded and contracted individually to create a desired chamber shape.

According to other illustrative embodiments, the invention is directed to a method for adjusting support to an anatomical location, the method including the step of adjusting the degree of expansion of an expandable chamber in a patient such that a tissue contacting upper surface of the expandable chamber is maintained in a position that discourages the anatomical site from rolling or sliding off of the upper surface. According to a further illustrative embodiment, the method includes adding and/or removing filler material to control a height/thickness of the expandable chamber. According to one illustrative embodiment, the method includes maintaining the upper surface in a substantially flat configuration. According to another illustrative embodiment, the method includes maintaining the upper surface in a substantially level configuration relative to the anatomical site. According to a further illustrative embodiment, the method includes maintaining a portion of a periphery of the expandable chamber at a greater height/thickness than an intermediate portion of the expandable chamber. According to another alternative embodiment, the method includes maintaining a substantially uniform height/thickness across the entire expandable chamber, except for example, for indentations in the upper and/or lower surfaces of the expandable chamber caused by internal interconnections between upper and lower sides of the expandable chamber.

According to another feature of the invention, the height of the expandable chamber may be adjusted while the patient is sitting and/or standing so that the torso is in a position in which most daily activities occur. Adjusting the sling tension while the patient's torso is substantially upright allows determining the most suitable support of the anatomical site (e.g., a patient's urethra) while the patient is engaged in everyday activities. The minimally invasive nature of the method of the invention makes such adjustment possible.

The invention described herein may be employed with various slings, sling assemblies, and delivery devices, sling assembly-to-delivery device association mechanisms, and implantation approaches. Without limitation, examples of the foregoing are disclosed in U.S. Pat. No. 6,042,534, entitled "Stabilization sling for use in minimally invasive pelvic surgery," U.S. Pat. No. 6,755,781, entitled "Medical slings," U.S. Pat. No. 6,666,817, entitled "Expandable surgical implants and methods of using them," U.S. Pat. No. 6,042,592, entitled "Thin soft tissue surgical support mesh," U.S. Pat. No. 6,375,662, entitled "Thin soft tissue surgical support mesh," U.S. Pat. No. 6,669,706, entitled "Thin soft tissue surgical support mesh," U.S. Pat. No. 6,752,814, entitled "Devices for minimally invasive pelvic surgery," U.S. patent application Ser. No. 10/774,826, entitled "Devices for minimally invasive pelvic surgery," U.S. patent application Ser. No. 10/774,842, entitled "Devices for minimally invasive pelvic surgery," U.S. patent application Ser. No. 10/939,191, entitled "Devices for minimally invasive pelvic surgery," U.S. patent application Ser. No. 10/460,112, entitled "Medical slings," U.S. patent application Ser. No. 10/092,872, entitled "Medical slings," U.S. patent application Ser. No. 10/093,371, entitled "System for implanting an implant and method thereof," U.S. patent application Ser. No. 10/093,398, entitled "System for implanting an implant and method thereof," U.S. patent application Ser. No. 10/093,424, entitled "System for implanting an implant and method thereof," U.S. patent application Ser. No. 10/093,450, entitled "System for implanting an implant and method thereof," U.S. patent application Ser. No. 10/093,498, entitled "System for implanting an implant and method thereof," U.S. patent application Ser. No. 10/094,352, entitled "System for implanting an implant and method thereof," U.S. patent application Ser. No. 10/631,364, entitled "Bioabsorbable casing for surgical sling assembly," U.S. patent application Ser. No. 10/641,192, entitled "Medical slings," U.S. patent application Ser. No. 10/641,376, entitled "Spacer for sling delivery system," U.S. patent application Ser. No. 10/641,487, entitled "Systems, methods and devices relating to delivery of medical implants," U.S. patent application Ser. No. 10/642,395, entitled "Systems, methods and devices relating to delivery of medical implants," U.S. patent application Ser. No. 10/642,397, entitled "Systems, methods and devices relating to delivery of medical implants," U.S. patent application Ser. No. 10/832,653, entitled "Systems and methods for sling delivery and placement," U.S. patent application Ser. No. 10/918,123, entitled "Surgical slings," and U.S. patent application Ser. No. 10/973,010, entitled "Systems and methods for sling delivery and placement," the entire contents of all of which are incorporated herein by reference.

What is claimed is:

1. A method of implanting a sling assembly comprising:
   implanting a sling assembly under a patient's bladder neck or urethra wherein the sling assembly comprises:
      a urethral support sling having first and second ends and an expandable chamber located intermediate to the first and second ends, the expandable chamber including upper and lower sides wherein:
      the upper side is substantially flat when the expandable chamber is inflated;
      the upper and lower sides are attached at one or more locations internal to the expandable chamber; and
      the one ore more locations include at least one through passage forming a perforation through the chamber, the perforation having at least one side wall extending between the upper side and the lower side and defining an external surface of the expandable chamber; and
   expanding the chamber.

2. The method of claim 1, wherein the through passage includes a resilient wall attaching the upper and lower sides.

3. The method of claim 2, wherein the through passage includes a wall attaching the upper and lower sides, the wall being configured to stretch as the chamber expands.

4. The method of claim 1, wherein the one or more locations include at least one divider extending between the upper and lower sides for dividing the expandable chamber into a plurality of sub-chambers in fluid communication with each other.

5. The method of claim 1, wherein the one or more locations includes at least one cord-like structure for attaching the upper and lower sides.

6. The method of claim 2, wherein the one or more locations include one or more side walls extending between the upper and lower sides and located along a periphery of the expandable chamber.

7. The method of claim 1, wherein the upper side of the expandable chamber is substantially rigid.

8. The method of claim 1, wherein the upper side of the expandable chamber is pre-shaped to fit the contour of the urethra.

9. The method of claim 1, wherein the expandable chamber includes a height adjustable side wall, attached at one edge to the upper side and at another edge to the lower side, and having an accordion-like structure.

10. The method of claim 9, wherein the height adjustable wall extends along a width of the expandable chamber.

11. The method of claim 9, wherein the height adjustable wall extends along a length of the expandable chamber.

12. The method of claim 1, wherein the expandable chamber is formed at least in part from a self-sealing material.

13. The method of claim 1 comprising a port for at least one of inserting and removing a filler material into or from, respectively, the expandable chamber.

14. The method of claim 13, wherein the port includes an extension tube for extending from the expandable chamber to a location remote from the expandable chamber for providing fluid access to the expandable at a location other than where the expandable chamber is located.

15. The method of claim 1, wherein the expandable chamber is sized and shaped for expansion by inserting at least one of a gas, liquid, gel, solid particles, particulate slurry, or a phase-changing material.

16. The method of claim 1, wherein the expandable chamber is sized and shaped for expansion with saline.

17. The method of claim 1, wherein the expandable chamber is sized and shaped for expansion with air.

18. The method of claim 1, wherein the expandable chamber is formed at least in part from a permeable material.

19. The method of claim 18, wherein the expandable chamber is sized and shaped for expansion with a therapeutic agent.

20. The method of claim 19, wherein the therapeutic agent includes at least one of a chemical, a biological, a growth factor, a genetic material, and a hormone.

21. The method of claim 1, wherein the sling is coated with a therapeutic agent.

* * * * *